United States Patent [19]
Ophir et al.

[11] 4,389,893
[45] Jun. 28, 1983

[54] PRECISION ULTRASOUND ATTENUATION MEASUREMENT

[75] Inventors: Jonathan Ophir; Nabil F. Maklad, both of Houston, Tex.

[73] Assignee: North American Philips Corporation, Tarrytown, N.Y.

[21] Appl. No.: 268,882

[22] Filed: Jun. 1, 1981

[51] Int. Cl.³ .............................................. G01N 29/04
[52] U.S. Cl. ....................................... 73/599; 73/600; 128/660
[58] Field of Search ................. 73/599, 600, 597, 602, 73/620; 128/660

[56] References Cited
U.S. PATENT DOCUMENTS 3,346,067 10/1967 Schroeder .............................. 73/599
4,138,999 2/1979 Eckhart et al. ....................... 73/599

Primary Examiner—Anthony V. Ciarlante
Attorney, Agent, or Firm—Daniel M. Rosen

[57] ABSTRACT

Method and apparatus for measuring an attenuation characteristic in a region of interest using ultrasound wherein two statistically independent set of values are accumulated as a difference between logarithms of pairs of each signal set, and the attenuation characteristic calculated as a central tendency parameter of each set of values.

12 Claims, 8 Drawing Figures

PRECISION ULTRASOUND ATTENUATION MEASUREMENT

BACKGROUND OF THE INVENTION

The invention relates to methods and apparatus for measuring in vivo ultrasound attenuation characteristics of limited regions of interest using a pulse echo mode.

The acoustic impedance of a material is the product of its density and the speed of acoustic waves therein. Whenever acoustic energy, such as ultrasound, passes through a boundary defined by a change in acoustic impedance, a portion of the energy is reflected, while the remainder passes through the boundary. In echo ultrasound technology, pulses of ultrasound energy are transmitted into a material for the purpose of producing echo signals for analysis. In medical diagnostics, ultrasound pulses are transmitted into the body. Internal tissue boundaries and inhomogeneities produce reflections of these pulses. The transit time of the reflected energy pulses and knowledge of the speed of sound propagation in tissue permit the determination of the depth of such reflections.

Aside from the echoes which are produced at boundaries where impedance changes, the tissue itself absorbs part of the ultrasound energy. The resultant attenuation of an ultrasound pulse as it passes through tissue is known to be roughly proportional to the frequency of the energy. Similarly structured boundaries and layers, located deeper in the tissue, thus produce weaker signals on account of the absorption of the incident as well as of the reflected signals. The local scattering in tissue varies in an unpredictable manner over small distances. The local attenuation of a single pulse of ultrasound energy is not, therefore, regarded as a meaningful or reproducible diagnostic measurement. Accepted ultrasound imaging techniques therefore rely on imaging boundaries, usually by modulating the intensity of pixels in a display in proportion to the intensity of reflected echoes from corresponding points in the body. Attenuation effects in tissue tend to distort such images. Most imaging systems incorporate some form of time-gain compensation to reduce artifacts attributable to tissue attenuation in the displayed images.

A first prior art technique for measuring ultrasound attenuation required that the material be placed between separate transmitting and receiving transducers. This technique is not considered practical for in vivo measurement in humans since ultrasound can not usually be propagated through the body. A second prior art technique utilized a known reflector to return pulses to a common transmitting/receiving transducer. It is not, however, considered a practical in vivo technique, since it is not usually practical or desirable to insert a reflector into the body. The abovedescribed techniques further measure an attenuation value which characterizes the entire path of the propagating energy and are not suitable for measuring attenuation at a limited region of interest along the path of propagating energy.

A current summary of medical ultrasound imaging, including the discussion of attenuation characteristics and various scan techniques is described generally in an article entitled "Medical Ultrasonic Imaging: An Overview of Principals and Instrumentation" by James F. Havlice and John C. Taenzer, appearing in the Proceedings of the IEEE, Vo.. 67, No. 4, April 1979 which is incorporated herein by reference.

Knowledge of the ultrasound attenuation characteristic within a limited region may have specific value for medical diagnostic purposes. It is known, for example, that diseased livers have different attenuation characteristics than healthy ones. Thus, a measure of attenuation within a region of interest including the liver may provide an indication of a diseased condition which is not otherwise detectable. In addition, attenuation values may be indicative of an origin of a tissue sample and may thus be useful for tissue identification. In tumor detection, the scattering of ultrasound by a tumor may be the same as that of healthy tissue, but the attenuation characteristics may be measurably different. Thus a measure of attenuation will provide additional data which is not utilized in current ultrasound images. Further, since in vivo study of tissue for absorption characteristics is not presently practical, the ability to make depthwise attenuation measurement with ultrasound scanner equipment may provide a further clinical basis for diagnosis.

BRIEF DESCRIPTION OF THE PRESENT INVENTION

The present invention measures local ultrasound attenuation within a region of interest. The rate at which ultrasound echoes decay with range along a given path is not in itself indicative of attenuation of the tissue in a region. It has been found, however, that the average rate at which statistically independent ultrasonic echoes decay in a region with range is indeed indicative of the attenuation coefficient of the tissue in that region. The present invention utilizes a technique of averaging a set of independent measurements of the logarithms of differential attenuation in the region, to produce the desired attenuation value. This may be done, in a C-scan configuration, by moving a transducer over a raster pattern in a single plane to acquire a statistical accumulation of data, resetting the transducer position to a lower depth, repeating the raster scan, applying logarithmic correction, calculating the mean value of each corrected data set, finding the difference between the means and dividing the difference by the interplanar spacing. The invention may also be practiced in a B-scan mode by taking a series of differences between logarithms of the amplitude of echoes from pairs of points on B-scan lines and generating the means of the series divided by the range between the points.

DESCRIPTION OF THE DRAWINGS

This specification is to be read in connection with the attached drawings in which.

DETAILED DESCRIPTION OF THE INVENTION

Figure 1:
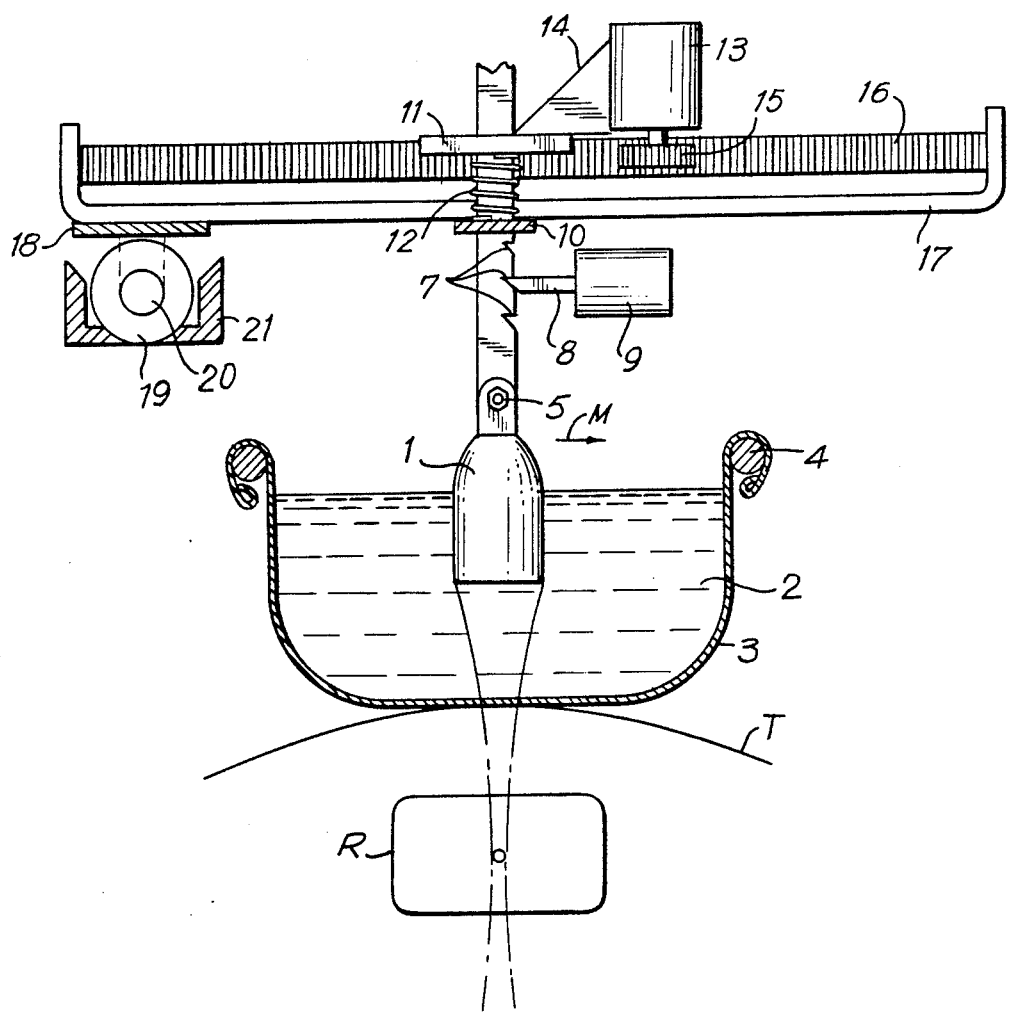
FIG. 1 is a mechanical configuration of a C-scanner.

With reference to FIG. 1, a mechanical configuration of a C-scanner is shown in detail. A tissue under examination, designated T, having a region of interest, R is positioned in general proximity of a single ultrasound transducer 1. The transducer 1 moves in a lateral direction, indicated by the arrow M, in a suitable acoustic medium such as water 2, which is contained within a flexible membrane 3, suspended from a collar 4. The transducer 1 is attached by means of an adjustable joint 5 to a vertical rod 6. The rod 6 contains a plurality of notches 7 at pre-set increments for the purpose of allowing the rod 6 and transducer 1 to have a vertical motion which is controlled by the retraction of the pin 8 into the solenoid 9. The vertical rod 6 is supported by a steel plate 10 and steel carriage 11, between which there is positioned a coil spring 12 for the purpose of applying a force against the solenoid pin 8. A stepping motor 13 provides the lateral drive to the transducer 1 and the vertical rod 6. The motor 13 is attached to the carriage 11 by a bracket 14. A pinion gear 15 is driven by the stepping motor in cooperation with a rack 16 which is in turn fastened to a carriage 17 and which rests on the support plate 18. The support plate 18 and its associated carriage are driven in a horizontal direction, normal to the lateral motion by a second stepping motor 19, driving a threaded shaft 20 upon which a plate 18 rides. The stepping motor 20 is supported within a frame 21 which is fixed to the overall mechanism of the scanner.

The transducer is utilized as both a pulse transmitter and a receiver. The pulse of energy propagates along a line through the tissue; echoes from increasing depths in the tissue are sequentially received by the transducer. The transducer converts the echoes into a sequence of electrical signals which represent the amplitude of corresponding echoes.

The speed of propagation of ultrasound in tissue may, for the purpose of this invention, be assumed to be constant. The time of arrival of an echo signal (measured with respect to the transmitted pulse), or range, thus corresponds to the depth of the echo-producing structure in the tissue. The signals from the transducer are time gated by a circuit which only passes signals from a predetermined depth in the region of interest. If the transducer is of the focussed type, the time-gate is preferably adjusted to only pass signals from echoes generated near the focal point of the transducer.

Ultrasound attenuation varies with frequency. The present invention characterizes attenuation in a narrow frequency band. Ideally the transmitted pulse should be narrow-band. However, this condition implies a relatively long pulse width, which inherently reduces the depth resolution. In a preferred embodiment a narrow-band pulse which consists of, for example, eight uniform cycles of radio-frequency ultrasound energy is utilized in conjunction with a wide-band receiver circuit. Alternatively a wide-band, short pulse which comprises for example, a single cycle of radio frequency ultrasound energy may be utilized in conjunction with a receiver which incorporates a narrow band-pass filter. The receiver may also be built with multiple narrow band-pass filters to simultaneously measure attenuation at several different frequencies.

Figure 3:
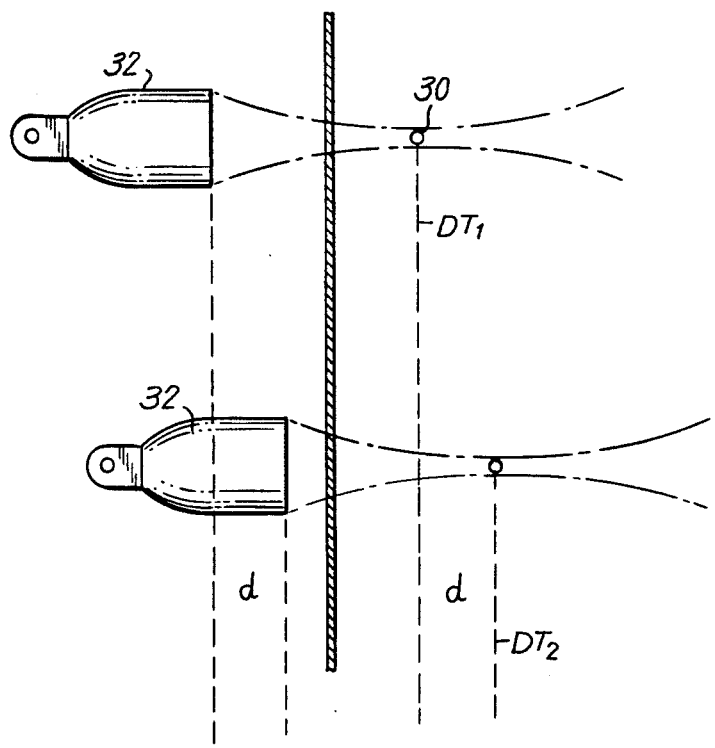
FIG. 3 illustrates the propagation of ultrasound in the C-scanner.
Figure 4:
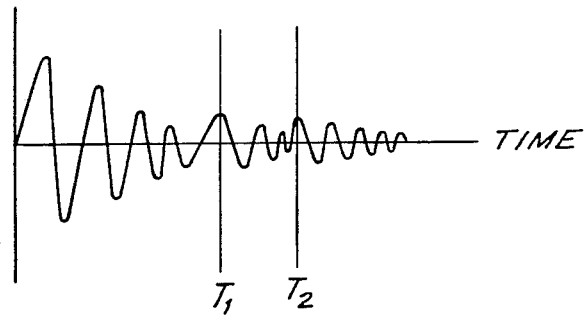
FIG. 4 shows electrical signals corresponding to echoes produced in the scanner of FIG. 3.

Measuring the local attenuation also requires that the effects of overlying tissue be compensated. In typical ultrasound scanners using time-gain compensation methods it is not possible to compensate for overlying tissue effects, except for the possibility of compensating for initial overlying tissue boundaries, such as the abdominal wall. This invention therefore employs the concept of differential measurements wherein multiple readings on different depths are taken. In operation the transducer is moved in a raster pattern to gather a first set of statistically independent signals which represent the amplitudes of echoes reflected from a first flat surface in the region of interest. The solenoid is operated to release the pin so that the transducer is lowered a predetermined distance into the water. The scanning operation is then repeated to measure a second set of statistically independent signals representing echoes from a second surface which is spaced at a constant depth, measured along the propagation path of the pulses, from the first surface. Thus, with reference to FIG. 3, a plurality of readings are taken along a planar section $DT_1$ at the focal point 3 of a beam generated by a transducer 32 and a second scan is employed in a different plane, designated $DT_2$. This is effected simply by re-positioning the transducer 32 at a different depth, with a differential d, thereby causing a focal point 30 of the beam to be positioned along the plane $DT_2$. It is also evident that a second data set can be derived from the echo train supply by recycling the lateral scan of the transducer and delaying the time-gate from $T_1$ to $T_2$, as shown in FIG. 4. However, this would not produce results as accurate as the former method since the beam may be of different intensity at the second position. In this case, use of delayed time-gating requires correction for transducer beam intensity. Re-positioning of the focal point 30 of the beam to a new depth provides the highest accuracy for data received for each plane.

Figure 5:
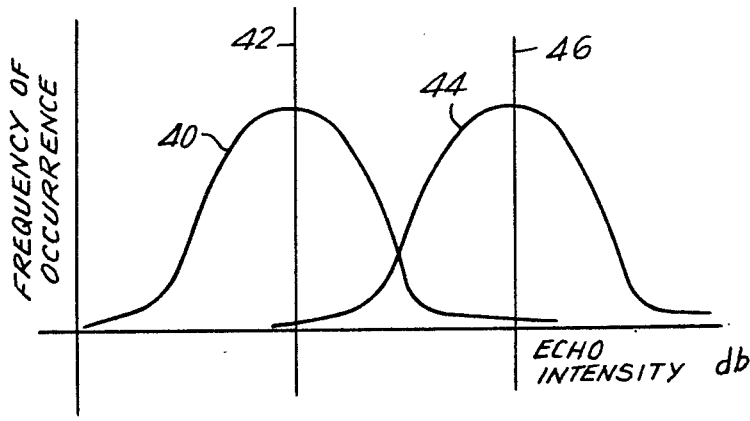
FIG. 5 shows a distribution of data gathered by the scanner of FIGS. 1-4.

The statistical distribution of measurement data at points along the plane $DT_1$ is generally illustrated in FIG. 5 by the first curve 40. The curve 40 is a histogram, having a central tendency area 42. A second statistical distribution of data at points in the plane $DT_2$ is illustrated by the second curve 44 having a central tendency at area 46. The curves 40 and 42 should be similar since they both represent a statistical distribution of points about two areas, one slightly displaced from the other in depth. The two curves are shifted, one from the other, along an axis representing echo intensity the added attenuation, resulting from the increase in penetration depth. A calculation of the difference between the statistical distribution of points on curves 40 and 44 over the dimensional depth d results in a normalized attenuation reading for the tissue between the two planes $DT_1$ and $DT_2$. Typical dimensional configurations for the respective planar areas of the region of interest can be a one centimeter by two centimeter rectangle, with data samples taken on two millimeter centers. The distance between data points should be no less than one half the focal spot size. In this example, as many as 1000 data points can be taken. A histogram showing a point distribution is shown in the attached appendix 1.

Figure 2:
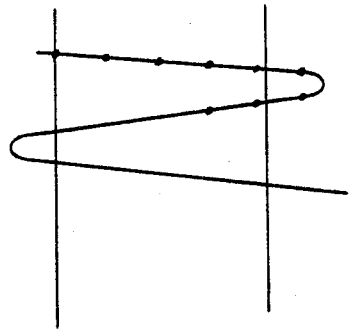
FIG. 2 illustrates the motion of a transducer during a C-scan of a plane.
Figure 6:
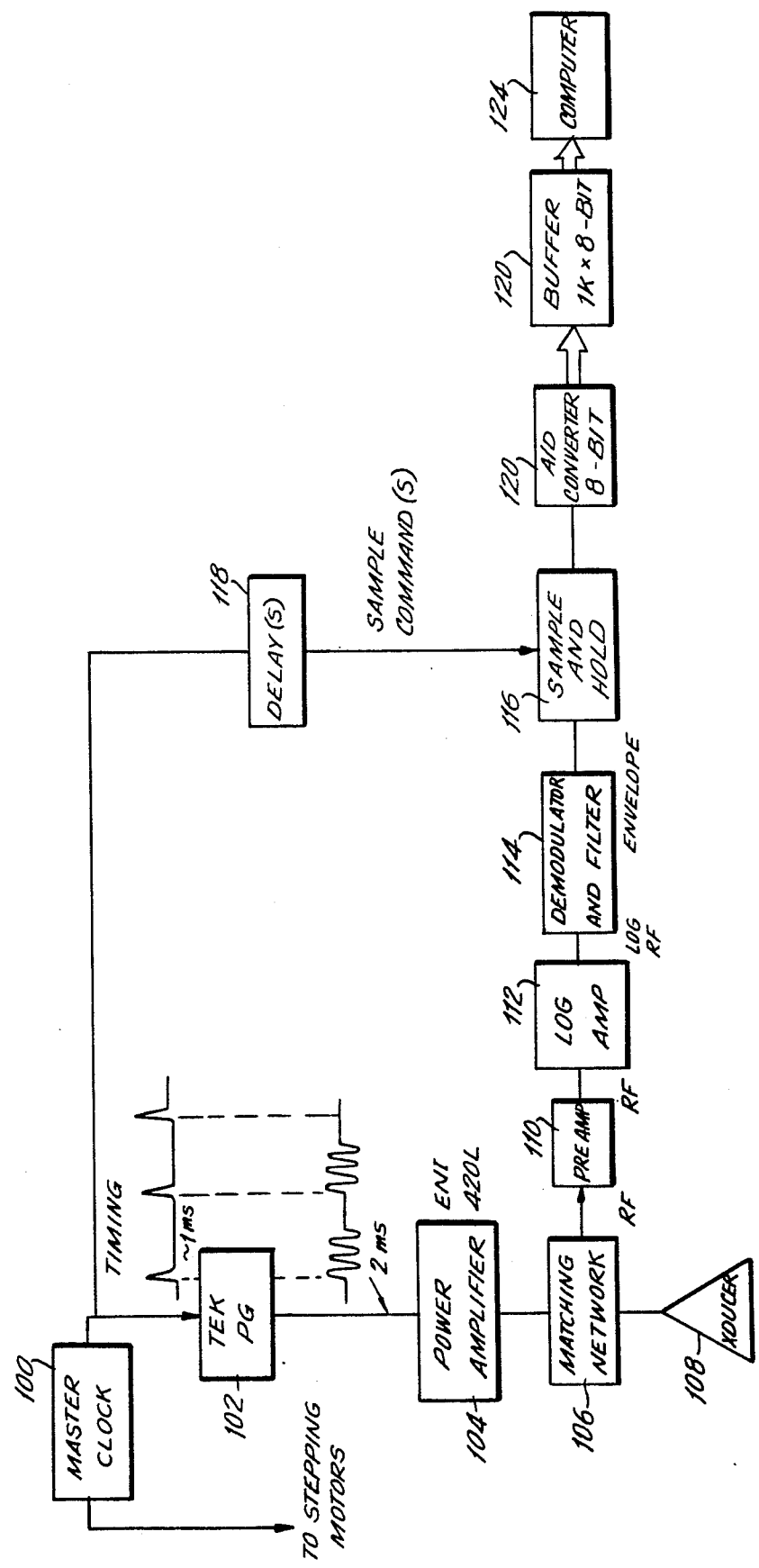
FIG. 6 is a block diagram of electronics for a C-scanner of the invention.

The number of points taken to determine an average sufficiently accurate for accuracy is a function of a number of parameters, such as focal spot size or sampling spot size, variation in echo intensity, total sample size, and the like. The distribution of data points in each plane can be characterized by any of the known statistical parameters which characterize central tendency, for example the mean (average), median, or mode. However, for ease of calculation, the mean (average) of the data points is the preferred central tendency parameter. If the samples from the first plane are designated $X_i$ where i equals 1, 2, 3 ... n, and the samples from the second plane are designated $Y_i$ where i equals 1, 2, 3 ... n, then the algorithm used to find the attenuation coefficient of the material contained between the planes is:

$$\alpha = \frac{1}{nd}\left[\sum_{i=1}^{n}\log x_i - \sum_{i=1}^{n}\log y_i\right]$$

where:
  $\alpha$ = the attenuation coefficient of the material and
  d = the spacing between the planes As shown in FIG. 6, a master clock circuit 100 provides driving pulses for the stepping motors 13 and 19, shown in FIG. 1, for the purpose of driving them in accordance with the desired scan pattern, such as shown, for example, in FIG. 2. Simultaneously, the master clock provides driving pulses for energizing a pulse generator 102. The driving pulses may be of approximately 1 or 2 microsecond duration and are spaced about one millisecond apart. This interpulse spacing is sufficient to allow a complete train of echoes to be received prior to transmitting the next pulse, and for all reverberation artifacts to subside. As a result of applying the drive pulses to the pulse generator 102, a burst of sinusoidal waves having a frequency in the range from 1 to 7 MHz, with 3 MHz to 5 MHz being preferable, is released to the power amplifier 104 which may be a conventional wide band power amplifier such as an EN14201, capable of handling a ten megahertz bandwidth. The output of the power amplifier is coupled to a matching and protection network 106, such as a transformer and diode array, conventionally designed, for the purpose of optimizing the power transferred between the power amplifier 104 and the transducer 108 and protecting the input of the receiving circuits from the output of the amplifier. For B-scan operation, it should be noted the burst sinusoidal waves produced by the pulse generator may be confined to a single cycle for the purpose of providing the necessary image quality required for B-scans.

The transducer 108 transmits the ultrasonic sound energy into the region of interest in the object and receives echoes based upon reflections within the region of interest. The matching network 106 provides the received signals to the preamplifier 110. Typically, the preamplifier has a wide dynamic range, in the range of 70 to 90 db, and is broadband. The output of preamplifier is fed into a log amplifier 112. A typical example of a log amplifier may be found in U.S. Pat. No. 4,145,741, the disclosure of which is incorporated by reference herein. It is important that the amplifier closely follow an ideal logarithmic gain characteristic. This may be assured by the manufacturer or the amplifier may be calibrated by pretesting and providing software corrections for each signal level over the entire dynamic range of the log amplifier to insure that any deviation is compensated in the production data. The output of the log amplifier 112 is coupled to a demodulator and filter 114, which removes the high frequency component of the echo signals and leaves an envelope signal. The resulting envelope is conducted to the sample and hold circuit 116 which is timegated by means of the predetermined delay set in the delay circuit 118 for gating the envelope at the desired intervals. These intervals represent the level equivalent of a depth of penetration from which echo signals have been received.

The amplitude of the log converted sample signals at each of the sample intervals is then digitized in a conventional manner by means of an analog to digital conversion circuit 120, and placed in a conventional 8 bit data word format. The data word is placed in a 1k×8 buffer 122, from which it is retrieved by computer 124 for data multiplication in accordance with the procedures previously discussed.

The measurement of data at predetermined time instants, based upon the previously noted assumption of a substantially constant speed of sound through the medium under examination, thereby provides an echo signal repesentative of a condition at a pre-determined depth.

The data set is maintained by the computer until all of the data on a common plane represented by changing lateral positions of the transducer is collected. The computer then determines central tendency parameters, which are characteristic of the data set measured in plane $DT_1$. The entire operation is repeated again with the transducer head repositioned for the plane $DT_2$. A central tendency parameter for that data is then derived, and the attenuation in the region calculated, in accordance with the algorithm set forth above, by subtracting or determining the difference between the central tendency parameter and in essence dividing by a time derived factor which represents the distance between the planes $DT_1$ and $DT_2$.

It is noted in accordance with the foregoing concept that all of the data at a predetermined depth is obtained, logarithmically corrected, and then averaged for a particular depth. Then a second set of data is defined for a different depth, logarithmically corrected, and a corresponding average performed. As a final step, the two averages are differenced and divided over the distance therebetween for determination of the attenuation characteristic. This technique is particularly adaptable to the C scan mechanism shown in connection with FIG. 1.

The correction of the logarithmic amplifier 112, noted above may be effected by means of software. A logarithmic amplifier may be analyzed over its entire dynamic range and each deviation, as well as interpolation points, calculated by appropriate digitization along the entire range. A suitable software correction routine, in the Basic computer language is attached hereto as Appendix No. 2.

The master clock and scanning motors may also operate under the control of the computer 124, and an exemplary routine for controlling such equipment, in the Basic language, is attached hereto as Appendix No. 2.

The accumulation of data along each surface, at a common time interval, and a plot in the nature of a histogram having a central tendency, such as is shown in its envelope form in FIG. 4, may be also effected by means of appropriate programming for the computer. An exemplary routine for accomplishing the foregoing, and for calculating the attenuation between the surfaces, in the Basic language, is attached hereto as Appendix No. 4.

Figure 7:
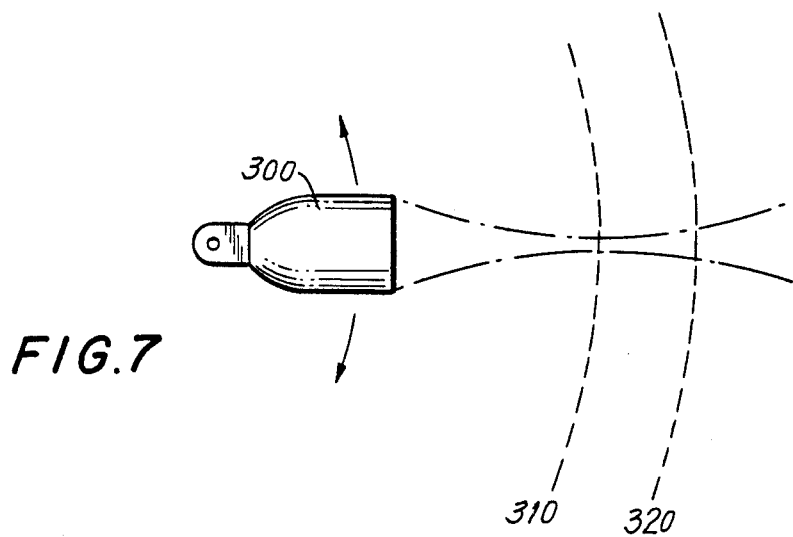
FIG. 7 illustrates a technique using a B-scan mode.

It is also possible to use the above described technique in a B-scan mode. If for example, the method is utilized with a B-scan mode sector scanner 300 (FIG. 7) the scanned surfaces are portions of cylinders 310 and 320. It is usually impractical to move the transducer to different depths in a B-scan environment so that a variable time gate, and if necessary compensation for transducer focus effects, should be provided. The sector scan transducer described in U.S. Pat. No. 4,092,867 is, for example, useful for a B-scan embodiment of the present invention.

It is also possible to collect multiple sets of data points along a single line generated by B-scanner transducer. In that case, the echo signals returned from a single pulse are sorted as a function of their time of arrival using range gating techniques. The signals are then paired; the signals in each pair representing two echoes whose times of arrival differ by a constant amount. The amplitudes of signals in each pair are logarithmically converted and the later signal subtracted from the earlier signal in the pair. A set of statistically independent difference values are collected along one or more lines in the region of interest and a central tendency parameter is determined for the distribution of values in the set. The attenuation characteristic is then calculated by dividing the value of the central tendency parameter by the difference in arrival times of the echoes in the pairs.

Figure 8:
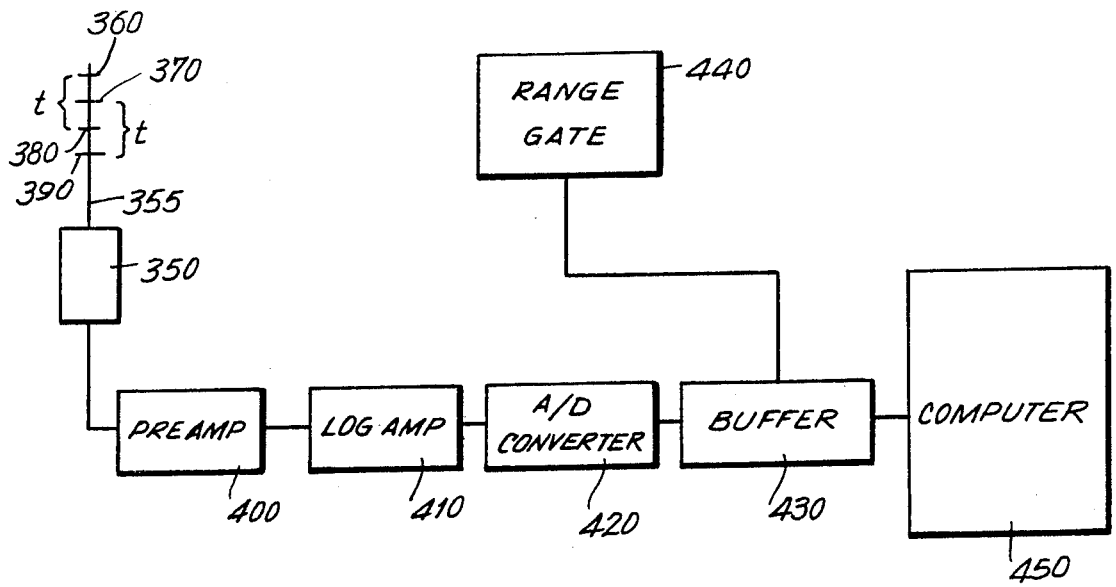
FIG. 8 is apparatus using a paired-pulse technique in a B-scan mode.

FIG. 8, illustrates apparatus for practicing the above-described method. A transducer 350 projects pulses and receives echoes along a B-scan line 355, echoes received by the transducer are processed in a pre-amplifier 400, log amp 410 and A-D converter 420 which may be the same units described in previous embodiments. Data words produced by the A-D converter are stored in a buffer 430 in separate location which correspond to their range along the B-scan line 355 under control of a range gate 400. The computer 450 selects pairs of words from the buffer which are, each time, separated by a constant range t along the line. Thus words representing echoes 360 and 380 constitute a first pair and words representing echoes 370 and 390 represent a second pair. The computer subtracts the word values and determines a central tendency parameter in a manner analogous to that described in Appendix 4.

The data accumulated in computer will thus represent a plurality of data values representing attenuations due to absorption characteristics at various points within the region under examination. The data may be employed as an attenuation map, thus providing a printout of attenuation differences, or may be employed as a table of values. Alternatively, the data may be employed on displays, in the nature of a B scan or brightness modulated display for indicating an attenuation distribution throughout a given region of interest. For example, by assigning different levels of attenuation to a 64 position gray scale, a contrast display may be provided on the face of the CRT. Alternatively, hard copy displays in the nature of x-ray images may be employed.

Other forms of utilization of data derived in accordance with the inventive method and apparatus will apparent to those skilled in the art.

What is claimed is:

1. A method of measuring an attenuation characteristic in a region of interest comprising:
 introducing pulses of ultrasound energy into the region;
 detecting narrow-band signals which represent the amplitude of echoes of said pulses which are reflected from different depths along a plurality of propagation paths within said region;
 accumulating a first statistically independent set of said signals which represent echoes from a first surface in said region;
 accumulating a second statistically independent set of said signals which represent echoes from a second surface in said region which is spaced at a determined distance, along said paths, from said first surface; and
 calculating an attenuation characteristic in said region as the difference between (1) a central tendency parameter of the logarithms of the signals in said first set and (2) the same central tendency parameter of the logarithms of the signals in the second set.

2. A method of measuring an attenuation characteristic in a region of interest comprising:
 introducing pulses of ultrasound energy into said region;
 detecting narrow-band signals which represent the amplitude of echoes of said pulses which are reflected from different depths along one or more propagation paths within said region;
 accumulating a set of statistically independent values which represent the difference between the logarithm of pairs of said signals, each pair of signals comprising echoes of the same pulse which propagate along a common path and which are separated from each other by a constant time interval; and
 calculating the attenuation characteristic as a central tendency parameter of said set of values.

3. An apparatus for measuring an attenuation characteristic in a region of interest comprising:
 means for introducing pulses of ultrasound energy into the region;
 means for detecting narrow-band signals which represent the amplitude of echoes of said pulses which are reflected from different depths along a plurality of propagation paths within said region;
 means for accumulating a first statistically independent set of said signals which represent echoes from a first surface in said region;
 means for accumulating a second statistically independent set of said signals which represent echoes from a second surface in said region which is spaced at a determined distance, along said paths, from said first surface; and
 means for calculating an attenuation characteristic in said region as the difference between (1) a central tendency parameter of the logarithms of the signals in said first set and (2) the same central tendency parameter of the logarithms of the signals in the second set.

4. An apparatus for measuring an attenuation characteristic in a region of interest comprising:
 means for introducing pulses of ultrasound energy into said region;
 means for detecting narrow-band signals which represent the amplitude of echoes of said pulses which are reflected from different depths along one or more propagation paths within said region;
 means for accumulating a set of statistically independent values which represent the difference between the logarithm of pairs of said signals, each pair of signals comprising echoes of the same pulse which propagate along a common path and which are separated from each other by a constant time interval; and
 means for calculating the attenuation characteristic as a central tendency parameter of said set of values.

5. The method of claim 1 or 2 or the apparatus of claim 3 or 4 wherein the central tendency parameter is the statistical mean.

6. The method of claim 1 or 2 wherein the energy is introduced in a B-scan mode.

7. The method of claim 1 or 2 wherein the energy is introduced in a C-scan mode.

8. The method of claim 1 or the apparatus of claim 3 wherein the surfaces are planar and are separated by a constant distance.

9. The method of claim 1 or 2 or the apparatus of claim 3 or 4 wherein the pulse comprises a plurality of cycles of ultrasound energy at a constant frequency.

10. The apparatus of claim 3 or 4 wherein the energy introduced comprises a wide-band pulse and wherein the means for detecting comprise at least one narrow-band filter.

11. The apparatus of claim 3 or 4 wherein the means for introducing comprises a sector scanner.

12. The apparatus of claim 3 wherein the means for detecting comprise a transducer; means for scanning a surface by moving the transducer in a raster pattern in a first plane; means for shifting the transducer to a second plane which is parallel to the first plane; and means for moving the transducer in a raster pattern in the second plane.

* * * * *

UNITED STATES PATENT AND TRADEMARK OFFICE
CERTIFICATE OF CORRECTION

PATENT NO. : 4,389,893
DATED : June 28, 1983
INVENTOR(S) : Jonathan Ophir and Nabil F. Maklad It is certified that error appears in the above—identified patent and that said Letters Patent is hereby corrected as shown below:

Col. 1, line 56, change "abovedescribed" to --above-described--.

Col. 4, line 45, after "intensity", insert --due to--.

Col. 6, line 9, change "multiplication" to --manipulation--.

Signed and Sealed this

Tenth Day of July 1984

[SEAL]

Attest:

Attesting Officer

GERALD J. MOSSINGHOFF
Commissioner of Patents and Trademarks